US009958522B2

United States Patent
Ruhm et al.

(10) Patent No.: US 9,958,522 B2
(45) Date of Patent: May 1, 2018

(54) METHOD FOR DETERMINING THE SPATIAL DISTRIBUTION OF MAGNETIC RESONANCE SIGNALS IN SUBVOLUMES OF AN OBJECT UNDER EXAMINATION

(75) Inventors: Wolfgang Ruhm, Ettlingen (DE); Johannes Schneider, Karlsruhe (DE); Peter Ullmann, Karlsruhe (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 1228 days.

(21) Appl. No.: 14/009,116
(22) PCT Filed: Apr. 18, 2012
(86) PCT No.: PCT/EP2012/057037
§ 371 (c)(1),
(2), (4) Date: Dec. 5, 2014
(87) PCT Pub. No.: WO2012/143369
PCT Pub. Date: Oct. 26, 2012

(65) Prior Publication Data
US 2015/0084627 A1    Mar. 26, 2015

(30) Foreign Application Priority Data
Apr. 20, 2011    (DE) .................... 10 2011 007 825

(51) Int. Cl.
*G01R 33/483*   (2006.01)
*A61B 5/055*    (2006.01)
(Continued)

(52) U.S. Cl.
CPC .......... *G01R 33/4833* (2013.01); *A61B 5/055* (2013.01); *G01R 33/246* (2013.01);
(Continued)

(58) Field of Classification Search
CPC .. G01R 33/246; G01R 33/385; G01R 33/561; G01R 33/4833; G01R 33/4836; G01R 33/5612; A61B 5/055
See application file for complete search history.

(56) References Cited

U.S. PATENT DOCUMENTS 7,847,549 B2 * 12/2010 Takahashi ............ A61B 5/0555
                                                324/307
7,999,545 B2 *  8/2011 Ullmann ............. G01R 33/4836
                                                324/309
(Continued)

OTHER PUBLICATIONS

Boernert, Peter et al., "Curved Slice Imaging" MRM 36:932-939, 1996.
Schneider, J.T. et al., "Enhanced Image Resolution and Reduced Measurement Time Using Inner Volume Imaging and Parallel Excitation", Proc. Intl. Soc. Mag. Reson. Med. 17, 2009.
Feinberg. D.A. et al., "Inner Volume MR Imaging: Technical Concepts and Their Application", Radiology 156, 1985, Pa. 743-747.
(Continued)

*Primary Examiner* — Dixomara Vargas
(74) *Attorney, Agent, or Firm* — Paul Vincent

(57) ABSTRACT

A method for determining the spatial distribution of magnetic resonance signals from at least one of N subvolumes predefines a reception encoding scheme and determines unique spatial encoding for at least one of the subvolumes but not for the entire volume under examination (UV). A transmission encoding scheme is also defined, wherein encoding is effected via the amplitude and/or phase of the transverse magnetization. The temporal amplitude and phase profile of the RF pulses is then calculated and each reception encoding step is carried out I times with variations according to the I transmission encoding steps in the transmission encoding scheme. The method makes it possible to largely restrict the spatially resolving MR signal encoding and image reconstruction to subvolumes of the object under examination without the achievable image quality sensitively depending on imperfections in the MR apparatus.

14 Claims, 9 Drawing Sheets

(51) Int. Cl.
  *G01R 33/561* (2006.01)
  *G01R 33/24* (2006.01)
  *G01R 33/385* (2006.01)

(52) U.S. Cl.
  CPC ....... *G01R 33/385* (2013.01); *G01R 33/4836* (2013.01); *G01R 33/561* (2013.01); *G01R 33/5612* (2013.01)

(56) References Cited

U.S. PATENT DOCUMENTS

| | | |
|---|---|---|
| 2009/0273345 A1 | 11/2009 | Ruhm |
| 2010/0066362 A1* | 3/2010 | Ullmann ............ G01R 33/4836 324/309 |
| 2010/0141252 A1 | 6/2010 | Fautz |
| 2010/0286500 A1 | 11/2010 | Ruhm |

OTHER PUBLICATIONS

Glover, G.H. "Phase-offset multiplanar (POMP) volume imaging: a new technique", J. Magn. Reson. Imaging 1, 1991, Pa. 457-461.
Pauly, J. et al., "A k-space analysis of small-tip-angle excitation", Journal of Magnetic Resonance 81, 1989, Pa. 43-56.
Ullmann, P. et al., "Single- and Multi-Voxel MR-Spectroscopy Using Parallel Excitation", Proc 17th Scientific Meeting, Intl Soc Magn Reson Med, Honolulu, 2009, Pa. 2602.
Katscher, U. et al., "Transmit SENSE", Magnetic Resonance in Medicine 49, 2003, Pa. 144-50.
Seifert, F. et al., "B1(+) steering by an adaptive 4-channel transmit/receive coil array", Proc 12th Scientific Meeting, Intl Soc Magn Reson Med, Kyoto, 2004, Pa. 1569.
Grissom, W. et al., "Spatial domain method for the design of RF pulses in multicoil parallel excitation", Magnetic Resonance in Medicine 56, 2006, Pa. 620-629.

* cited by examiner

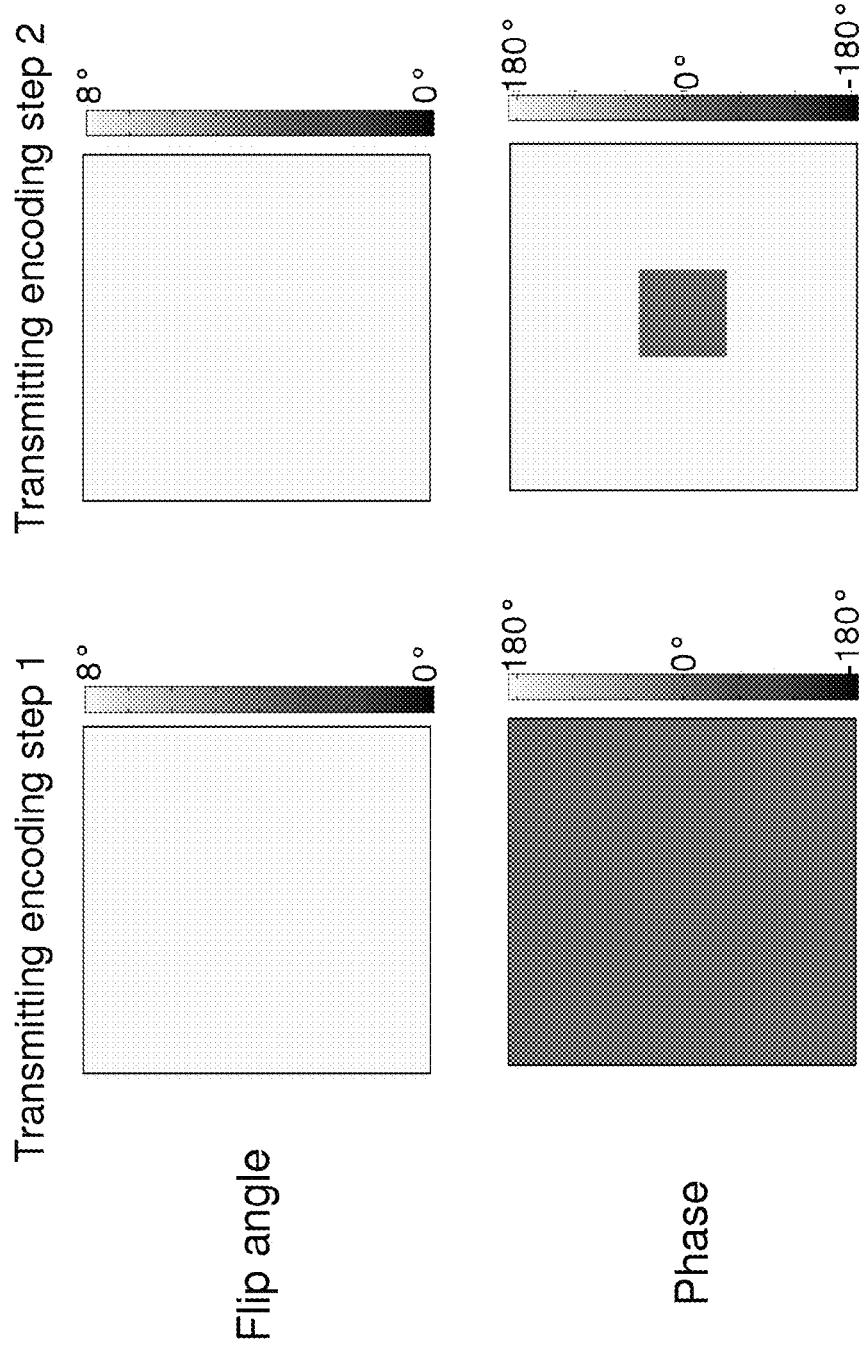

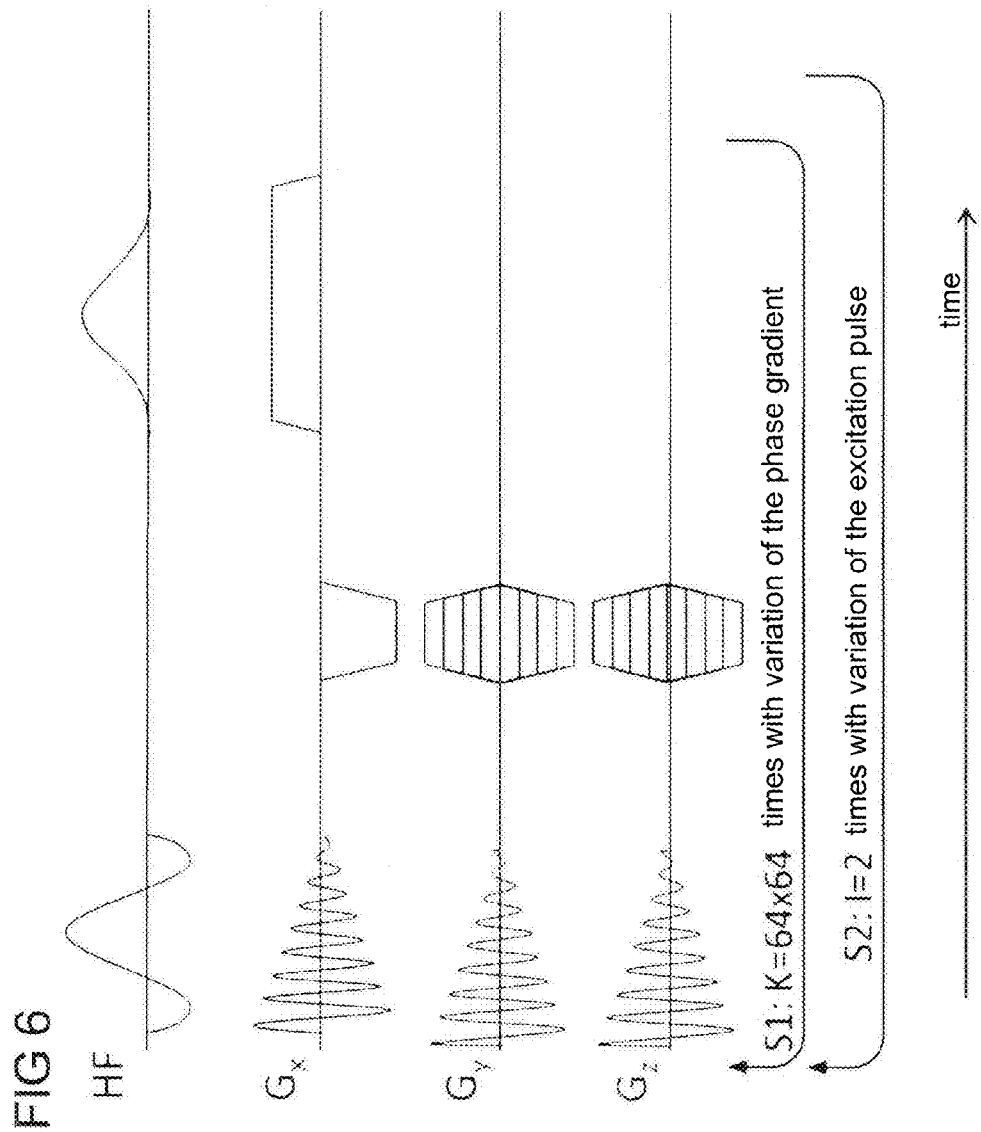

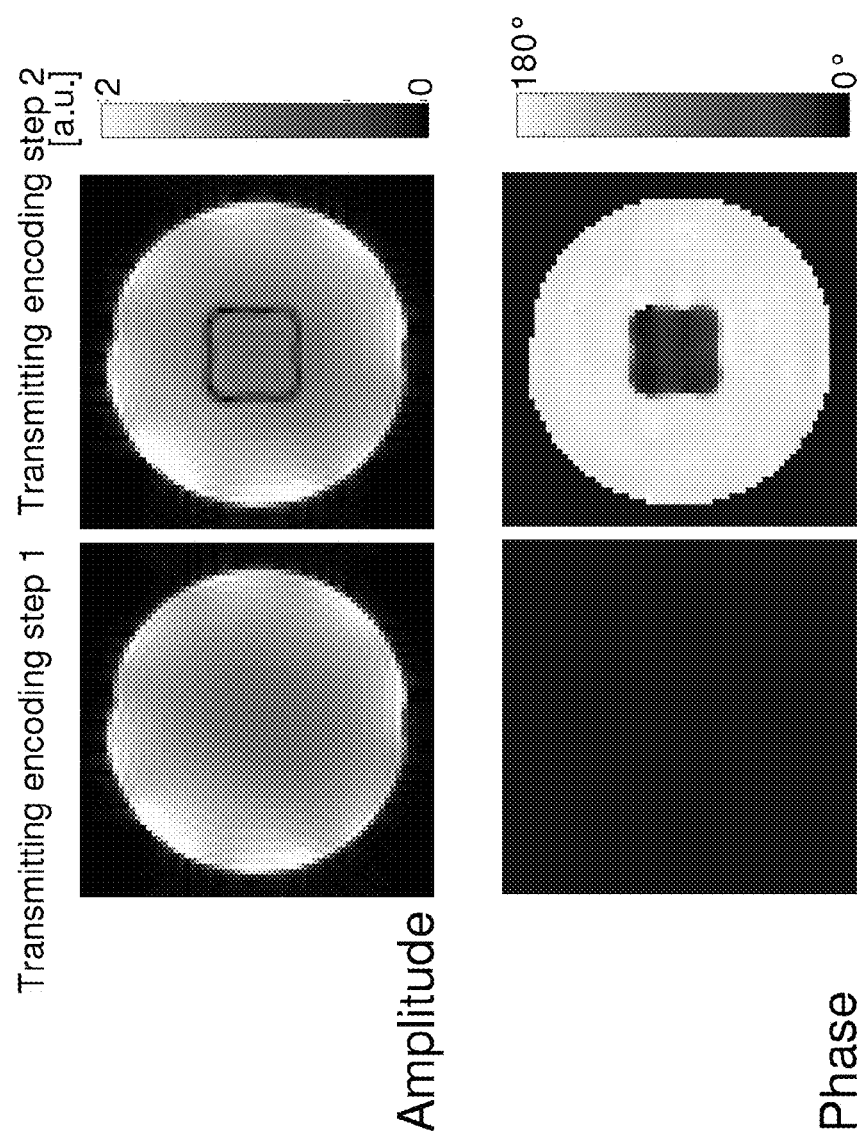

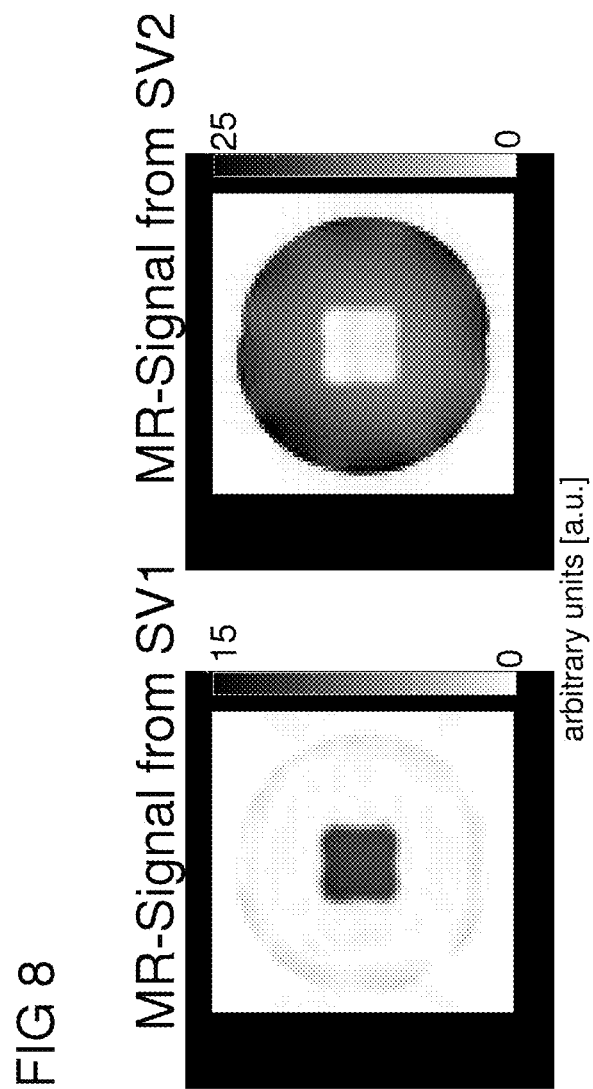

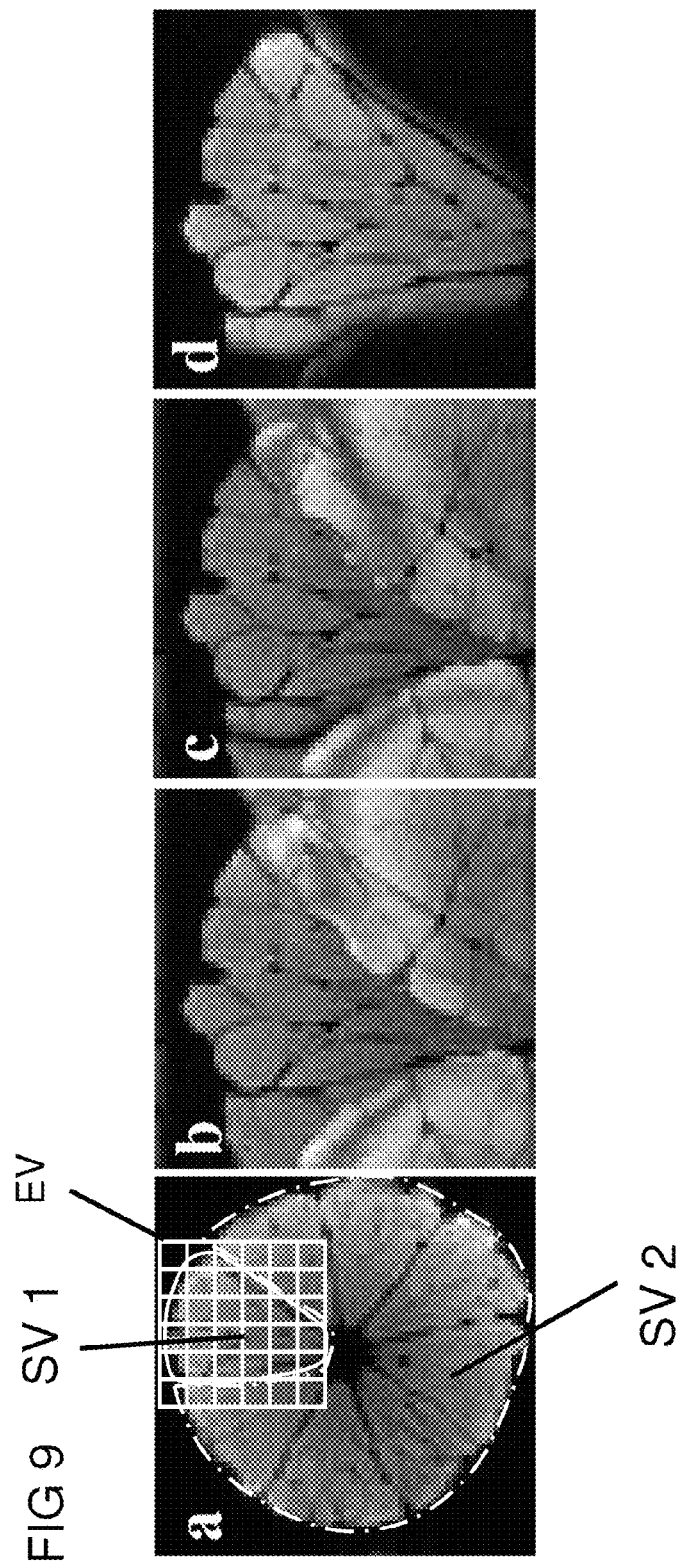

ically constant gradients
METHOD FOR DETERMINING THE SPATIAL DISTRIBUTION OF MAGNETIC RESONANCE SIGNALS IN SUBVOLUMES OF AN OBJECT UNDER EXAMINATION This application is the national stage of PCT/EP2012/057037, filed Apr. 18, 2012 and also claims Paris convention priority from DE 10 2011 007 825.8, filed Apr. 20, 2011.

The invention relates to a method for determining the spatial distribution of magnetic resonance signals from one or more non-overlapping subvolumes of an object under examination in the measurement volume of a magnetic resonance apparatus.

Such a method is known from [1].

In the method known from [1], a reception encoding scheme for spatial encoding of the magnetic resonance signals is used to reduce the measurement duration and/or to improve the spatial resolution, which defines unique spatial encoding in at least one dimension only for limited partial regions of the object under examination. The necessary uniqueness of spatial allocation of the received magnetic resonance signals is achieved by irradiating spatially selective radio-frequency pulses during execution of each spatial encoding step of the reception encoding scheme to excite transverse magnetization, which limit transverse magnetization contributing to subsequent signal acquisition within the object under examination to a subvolume to be mapped, which is located inside a uniquely encodable subregion. For that reason, during signal acquisition following each encoding step, only those magnetic resonance signals are measured that were caused by the nuclear spins located in the subvolume. After this, in a reconstruction step, one or more spatial distributions of the magnetic resonance signals within the subvolume to be mapped or the resulting quantities are calculated and the results of the reconstruction step are stored and/or displayed. Restriction to the selected subvolume has the advantage that the effort for spatial encoding can be correspondingly restricted, which can be used in classic spatial encoding methods to shorten the measurement duration for the same spatial resolution, to improve the spatial resolution for the same measurement duration, or to combine these advantages.

Magnetic resonance imaging (MRI), also termed magnetic resonance tomography (MRT), is a widespread technique for non-invasive acquisition of images of the interior of an object under examination and is based on the spatially resolved measurement of magnetic resonance signals from the object under examination. By subjecting the object under examination within the measurement volume of a magnetic resonance apparatus to an essentially static and homogenous magnetic basic field, also termed the main magnetic field, nuclear spins contained in it are oriented in the direction of the basic field, usually selected as the z-direction of a magnet-bound coordinate system. The associated orientation of the magnetic dipole moments of the atomic nuclei results in magnetization within the object under examination in the direction of the main magnetic field, which is termed the longitudinal magnetization. In the case of an MR examination (MR: magnetic resonance), irradiation of electromagnetic RF pulses (RF: radio frequency) by means of one or more RF transmission antennas, hereinafter also referred to as transmission elements of an RF transmission antenna device, excites this magnetization within the object under examination to effect precession movements whose frequencies are proportional to the local magnetic field strength. The magnetization vector is deflected from the equilibrium orientation (z-direction) by an angle hereinafter referred to as the flip angle.

In the MRI methods in use today, spatial encoding is imposed on the precession movements of the nuclear spins for all three spatial directions by time-variable superposition of additional position-dependent magnetic fields, hereinafter referred to as additional magnetic fields. These additional magnetic fields usually exhibit essentially constant gradients of the z-components in the spatial directions x, y and z within the object under examination and are produced by a coil configuration, termed a gradient system, that is controlled by one gradient channel for each spatial direction. However, for some years, various imaging techniques have existed, which also use non-linear additional magnetic fields with spatially varying gradients. Where magnetic fields are described hereinafter as linear or non-linear, this refers, unless stated otherwise, to the spatial dependence of the z-component of the additional magnetic fields. The spatial encoding is usually described according to a scheme in a space, called k-space that is conjugated with respect to real space by means of a Fourier transformation. In this k-space formalism, which can only be applied to the use of magnetic fields with gradients that are constant in space, it is possible to describe the switching of additional magnetic field pulses as a progression along a trajectory in k-space, termed the k-space trajectory.

The transverse component of the precessing magnetization associated with the nuclear spins, hereinafter also referred to as transverse magnetization, induces electrical voltage signals, which are also known as magnetic resonance signals (MR signals), in one or more RF reception antennas surrounding the object under examination and hereinafter referred to as RF reception elements of an RF reception antenna device. By means of pulse sequences (or measurement sequences) that contain specially selected sequences of RF pulses and additional magnetic field pulses (brief application of additional magnetic fields that are constant or variable over time), time-variable magnetic resonance signals are produced in such a way that they can be converted to the corresponding spatial representations. This is done according to one of many well-known reconstruction techniques after the MR signals have been acquired, amplified, and digitized using an electronic reception system, and processed using an electronic computer system, and stored in one-dimensional or multi-dimensional data sets. The pulse sequence used typically contains a sequence of measurement operations, termed encoding steps, in which the gradient pulses can be varied according to the chosen spatial encoding scheme. An encoding step usually comprises excitation of nuclear spins, at least one spatial encoding, and acquisition of the MR signals.

In conventional MR imaging, the nuclear spins to be examined are excited simultaneously in the entire object under examination and their spatial location is effected by superposition of spatially dependent phase and/or frequency encoding onto their precession movement. The spatial encoding is superposed by means of additional magnetic field pulses by applying so-called phase (encoding) gradients in a phase encoding period following RF excitation in time, in which a position-dependent phase change of the precession movement occurs and during signal readout by applying a so-called readout gradient, whereby spatially dependent modulation of the precession frequency is effected. Both encodings are usually based on an encoding scheme that permits determination of the spatial distribution of the magnetic resonance signals by means of a Fourier transformation. For special objectives, however, other image construction methods are applied.

Where RF reception antenna equipment with multiple reception elements with different spatial reception profiles is used, the spatial information contained therein can also be used for the spatial encoding of the received MR signals. Usually, this so-called sensitivity encoding is implemented in combination with phase and/or frequency coding, and there are many different methods for image reconstruction of MR signals encoded in this way.

Whenever a spatial encoding scheme is referred to below, a measurement rule is meant in which one or a combination of the known spatial encoding methods is applied and which permit, for MR signals measured in this way within a specific part of the measurement volume, unique spatial allocation of MR signal components with a particular spatial resolution. In principle therefore, the extent to which a certain volume element (pixels or voxels) of the object under examination contributes to the MR signal is determined from the MR signals measured in all encoding steps. Whenever the terms "spatially resolved" or "spatially resolving" are used below, this refers to the characteristic that there are at least two positions to which MR signal components can be uniquely assigned. In practice, in spatially resolved reconstruction, components of acquired MR signals are assigned to the pixels or voxels of an image matrix to be generated.

Spatially selective excitation is a technique widely used in magnetic resonance imaging, whose purpose is to spatially limit the transverse magnetization generated by excitation and/or to spatially vary their amplitude and phase in the excitation volume. The same applies to spatially selective inversion and spatially selective refocusing, wherein RF pulses with other functions as part of a pulse sequence are equipped with spatially selective properties in an analogous manner. In slice selection, the most frequent type of selective excitation, inversion, and refocusing, the excitation volume, inversion volume, and/or refocusing volume is reduced to a defined slice. In volume-selective MR spectroscopy (MRS), as well, selection of an area of examination, which is usually small compared with the object under examination as a whole, is customarily based on slice-selective excitation and refocusing pulses, wherein the spatial selectivity is successively generated in one spatial direction only, by means of a corresponding gradient pulse.

For multiple slice acquisitions, MRI and MRS methods have been developed, in which multiple, essentially parallel slices with different phase encoding are excited in multiple phase encoding steps and their magnetic resonance signals acquired. The signals are assigned to their corresponding excitation slice [2] using suitable data reconstruction, for example, Hadamard transformation.

Multi-dimensional, spatially selective excitation by means of multi-dimensional RF pulses [3], in which the excitation volume is restricted in more than one direction and/or the excitation is modulated in more than one direction, has also yielded numerous applications. These include excitation of a small three-dimensional volume or several volumes simultaneously within a much larger object under examination for localized spectroscopy, the mapping of a selectively excited region (ROI: region of interest) with a reduced field of view (FOV) with the aim of reducing the measurement time, the excitation of special volumes adapted to structures of the object under examination, or echo-planar imaging with reduced echo train lengths. The amplitude and phase modulation of the transverse magnetization in the excitation can also be used to compensate for disadvantageous effects of a non-homogeneous magnetic transmission field ($B_1$ field) of the RF transmission antennas used for excitation. This is an application that has become considerably more important today due to the large increase in high-field MRI systems on which such non-homogeneities occur especially frequently. In addition to its use for excitation, multi-dimensional RF pulses can also be used for spatially selective inversion or refocusing of the magnetization.

MRI and MRS methods are also known in which nuclear spins within one or more spatially separated areas under examination, and only there, are simultaneously excited selectively by means of multidimensional RF excitation and, during this excitation, a phase encoding is superposed onto the magnetic resonance signals by means of a suitable encoding scheme, which if the magnetic resonance signals of all areas under examination are acquired simultaneously, permits separation of the signals according to the area they originate from and/or determination of their spatial distribution within these areas [4].

According to the method disclosed in [5], it is also possible to create phase patterns of transverse magnetization during excitation in order to achieve partial or full spatial encoding of the magnetic resonance signals during excitation. By repeating excitation with different phase patterns as defined by a phase encoding scheme, an entire data set is collected in multiple phase encoding steps, which is then reconstructed spatially resolved according to the spatial encoding scheme and which provides, for example, two- or three-dimensional images of the object under examination. This method of spatial encoding will hereinafter be referred to as excitation encoding. Analogously, this method of spatial encoding with RF transmission phases can also be applied with spatially selective inversion or refocusing. Generally, the term transmission encoding will be used from now on when spatial encoding of the magnetization is generally applied during irradiation of spatially selective RF pulses.

For the practical use of mufti-dimensional RF pulses, a further aspect of technical progress of the past few has years has proven advantageous, which is described in detail in [6]. In the past, the spatially selective excitation was initially performed using a single RF transmission antenna with an essentially homogeneous transmission field ($B_1$ field) in conjunction with the gradient system. Inspired by the success of parallel imaging, in which signal acquisition is performed with RF reception antenna equipment with multiple reception elements, also termed antenna array in the specialist literature, it has now become customary to also use such RF transmission antenna devices, which consist of multiple transmission elements operated on multiple, independent RF transmission channels of the MR apparatus, for transmission in spatially selective excitation. In this way, it is possible to partially replace the spatial encoding, which in the case of multi-dimensional RF pulses by analogy with data acquisition is implemented by varying additional magnetic fields, with so-called sensitivity encoding and thus to reduce the length of the excitation pulses. This enables use of the different spatial variations of the RF transmission fields of the individual array elements, hereinafter also referred to as transmission profiles.

Because, in the case of one-channel transmission, the length of selective excitation pulses is usually one of the criteria limiting the applicability of this technique, parallel excitation (PEX) or mufti-channel excitation is a promising approach by which spatially selective excitation may be deployed more widely than it has been. Spatial encoding during transmission of RF pulses for the purpose of selective excitation, hereinafter referred to as spatial RF pulse encoding, enables the amplitude and phase of the transverse magnetization produced during transmission to be set depending on the location. This spatial RF pulse encoding differs both from classic acquisition spatial encoding, hereinafter referred to as reception encoding, which is performed without RF injection as part of data acquisition in a period following the excitation, in particular, during data acquisition (e.g. as phase, frequency, or sensitivity encoding), and also from the transmission or excitation encoding mentioned above, in which spatial-encoding amplitude or phase distributions of the transverse magnetization of the nuclear spins are generated in multiple encoding steps by means of spatially selective RF pulses.

One of the basic issues when using spatially selective excitation is determination of the RF pulses to be replayed by the transmission antenna device to generate the desired excitation pattern in conjunction with additional magnetic fields, e.g. by describing a k-space trajectory. In [3], Pauly et al. describe a method for single-channel spatially selective excitation with which, by a mathematical analogy of the selective excitation with Fourier imaging, the pulse form $B_1(t)$ to be attained can essentially be calculated by Fourier transformation of the desired excitation pattern and sampling of the Fourier transform along the prescribed k-space trajectory. Katscher et al. extend this calculation method to cover an antenna array with multiple independent transmission channels [6].

Besides this method of spatially selective excitation, which is characterized in that during excitation of the nuclear spin with RF pulses, simultaneously additional magnetic field pulses with a spatial-encoding effect are applied, techniques have also been developed by which, without the additional action of gradient fields, a spatial amplitude and/or phase modulation of the transverse magnetization is achieved by pure superposition according to the configured RF pulses, which are simultaneously irradiated with at least 2 transmission antenna elements [7].

Within the scope of the inventive method, a spatially selective radio frequency pulse refers to the totality of all RF pulses that are simultaneously irradiated via one or more transmission channels, which, due to their degrees of freedom, make it possible to implement different modifications to the magnetization state at different locations in the object, irrespective of whether this is performed in combination with pulses of spatial encoding additional magnetic fields or not. The combination of RF pulses with additional magnetic field pulses, refers to both simultaneous irradiation of RF pulses and application of additional magnetic fields as well as the interleaved application of additional magnetic fields and RF pulses. An RF pulse comprises at least one RF waveform, wherein each RF waveform is radiated by exactly one transmission element and can be described by a temporal amplitude and phase profile.

A typical feature of conventional MRI is that the entire part of the object under examination that is located in the measurement volume of the MR apparatus is excited and/or that slice-selective RF pulses limit the volume under examination in one dimension and that the reception encoding schemes must entirely spatially encode the object under examination in at least two dimensions, because nuclear spins from all parts of the volume under examination generally contribute to the acquired MR signals. Otherwise, non-spatially encoded signal components would cause image artifacts and other worsening of mapping accuracy and image quality. Because in many cases MRI examinations are only interested in relatively small parts, which are often located deep inside the object under examination, for example, in the case of in-vivo examinations, internal volumes defined by certain organs, and the additional time required to spatially encode the remaining volume under examination is considerable and does not, strictly speaking, contribute to the objectives of the examination, it is desirable to be able to employ methods that essentially limit image encoding and reconstruction as far as possible to the volume(s) of actual interest, referred to below as RoI(s) (Region(s) of Interest).

As already mentioned, a known method of achieving this objective is to limit the excitation of the nuclear spins to the RoI(s) using spatially selective RF pulses, apply the spatial encoding scheme in such a way that these RoI(s) are just about covered and only these RoI(s) are mapped, with a correspondingly shorter measurement duration and/or increased spatial resolution.

A disadvantage of this inventive method is initially the necessity to prevent, as far as possible, any MR signals from being generated outside the RoI(s) during RF excitation, since any residual signal could contribute to falsifying the image. This necessity makes the highest demands on the MR apparatus because, as practical experience has shown, even small imperfections during execution of the measurement sequence result in errors in the spatially dependent form of the excited transverse magnetization. Sources of error include, for example, inhomogeneity of the basic field, eddy current effects during creation of the additional magnetic field pulses and synchronization imprecision during generation of the RF and additional magnetic field pulses.

Moreover, in different MRI measurement sequences, the very different formation of a dynamic steady state of magnetization in the different areas of the volume under examination is disadvantageous. These differences are caused by the strongly diverging flip angles inside and outside the RoI and by the inhomogeneities of physical parameters of the object under examination, for example, relaxation times. It is therefore desirable to generate similar dynamic steady states of magnetization inside and outside of the selected RoI in order to make the spatially selective pulses more independent of the local properties of the object under examination and of the measurement apparatus.

The object of the invention is therefore to provide an MR measurement and reconstruction method that makes it possible to largely restrict the spatially resolving MR signal encoding and image reconstruction to one or more selected subvolumes of the object under examination without the achievable quality sensitively depending on imperfections in the MR apparatus.

SUMMARY OF THE INVENTION

This object is achieved with a method according to claim 1, wherein for determining the spatial distribution of magnetic resonance signals from at least one of N non-overlapping subvolumes of an object under examination in the measurement volume of a magnetic resonance apparatus, where N≥2, wherein
 in a preparation step,
  a measurement sequence with encoding steps is selected, wherein each encoding step contains the irradiation of one or more spatially selective RF pulses, by means of which one magnetization change is effected in each encoding step;
  the N subvolumes, N≥2, are selected such that, together, they completely cover at least one volume under examination, wherein the volume under examination corresponds to the part of the object under examination in which nuclear spins excited during execution of the selected measurement sequence contribute to at least one of the acquired MR signals, a reception encoding scheme with K reception encoding steps, K≥1, is specified, which defines unique spatial encoding in at least one spatial dimension for at least one of the subvolumes, wherein, however, this spatial encoding is not unique for the entire volume under examination in at least one of these dimensions a transmission encoding scheme with I transmission encoding steps is defined, where I≥N≥2, wherein encoding is effected via the amplitude and/or phase of the transverse magnetization defined spatially dependently by means of the magnetization change and for each of these I transmission encoding steps, the magnetization change is defined such that, at no position within each subvolume, the same encoding is defined as at another position within another subvolume and that, in at least one transmission encoding step in at least two of the subvolumes, excited nuclear spins contribute to the acquired magnetic resonance signal; and the temporal amplitude and phase profile of the spatially selective RF pulses to be irradiated to effect the magnetization changes is calculated;

in an execution step to carry out all encoding steps, each reception encoding step, which is defined according to the reception encoding scheme, is executed I times with variations according to the I transmission encoding steps of the transmission encoding scheme, wherein, in each encoding step, all RF pulses calculated for each transmission encoding step of the transmission encoding scheme are applied by means of at least one transmission element and, not overlapping in time with this or these RF pulses, spatial encoding is effected according to a reception encoding scheme, and magnetic resonance signals are acquired by means of at least one reception element;

in a reconstruction step based on the transmission encoding scheme, components of the acquired magnetic resonance signals are assigned to the N subvolumes and, for at least one of the subvolumes, which were spatially encoded according to the reception coding scheme, one or more spatial distributions of the magnetic resonance signals is/are reconstructed from the acquired magnetic resonance signals and/or variables derived from these are calculated, wherein this or these subvolumes are hereinafter referred to as mapping volumes, and in a result step, the results of the reconstruction step are stored and/or displayed.

The invention therefore relates to a method for determining the spatial distribution of magnetic resonance signals from one or more RoI(s) within an object under examination, wherein by limiting the imaging to these RoI(s), the measurement duration and/or increase in the image resolution can be achieved, and by encoding using spatially selective RF pulses, MR signals acquired outside the RoI(s) can be excluded from image reconstruction and the MR signals from each individual RoI can be assigned to that RoI, so that the reception encoding scheme on which image reconstruction is based only needs to be unique for the union of all RoIs or a part of them or, in the case of multiple RoIs, the encoding effort during measurement can even be reduced to the effort required for a single RoI.

The basic idea of the invention:

At least 2 non overlapping subvolumes of the object under examination are selected, which can be of any shape or size and together fully cover the volume under examination, wherein the volume under examination corresponds to the part of an object under examination inside the magnetic resonance apparatus, in which nuclear spins excited during execution of the selected measurement sequence contribute to the acquired MR signals.

One or more of these subvolumes are selected such that they each cover one or more of the RoI(s) for which a spatially resolved measurement is to be performed, for example, to generate a two- or three-dimensional image of the spin density. A reception encoding scheme is selected for the subvolume(s) selected for mapping, the so-called mapping subvolumes, which does not allow the entire volume under examination to be mapped in a spatially resolved manner. In order to keep the measurement duration as short as possible, this spatial encoding scheme should only realize spatial resolution encoding with predefined spatial resolution for a range that just about covers the mapping volume. If multiple mapping volumes are selected, it is advantageous in terms of measurement duration to select a reception encoding scheme whereby each of the mapping volumes is uniquely spatially encoded, but the union of all mapping volumes is not uniquely spatially encoded. The mapping volumes together constitute the so-called inner volume, the remaining subvolumes constitute the so-called outer volume. In most cases, it is advantageous to select a single subvolume as the outer volume.

A second encoding scheme, the transmission encoding scheme, is chosen with at least N encoding steps with which all MR signals from the volume under examination are encoded during measurement with irradiation of spatially selective RF pulses such that during subsequent reconstruction the totality of signals of all encoding steps can be broken down into N components, each of which can be assigned to one of the N subvolumes. According to this transmission encoding scheme, a magnetization change is defined for each of the N encoding steps and for at least the entire volume under examination. The change in magnetization is defined as the distribution of change of the transverse magnetization, which can be effected in one transmission encoding step with one or more spatially selective RF pulse(s). For each location within the volume under examination, the MR signals generated there are to be identified in amplitude and/or phase across the N encoding steps according to the transmission encoding scheme such that the encoding generated in this way can be uniquely assigned to a subvolume. It is advantageous to encode all positions within each subvolume in the same way with the transmission encoding scheme, but positions in different subvolumes differently. For each transmission encoding step, at least one spatially selective RF pulse specific to this encoding step is calculated, which, when irradiated, effects the change in magnetization for this encoding step.

When measurement is executed, multiple encoding steps are performed, which are defined by the interleaved execution of the transmission and reception encoding steps. In this case, each encoding step according to the reception encoding scheme must be executed N times according to the transmission encoding scheme, wherein, in the case of the repetitions according to the transmission encoding scheme, only the irradiated spatially selective RF pulses are varied according to the preliminary calculations for each of the I encoding steps. The order in which the individual encoding steps are performed is not predefined.

During data reconstruction, the MR signal components are separated out of the outer volume. Spatially resolved reconstruction is only performed for the inner volume, i.e. the selected mapping volumes, for example, calculation of two- or three-dimensional images. Here, too, the order is not defined. For example, image reconstruction can first be performed for each mapping volume and then any foldover that usually occurs can be removed by reconstruction according to the transmission encoding scheme.

Further variants and further advantageous characteristics and embodiments are described in the dependent claims.

In a variant of the inventive method, the transmission encoding scheme only defines the spatially dependently amplitude of the transverse magnetization to be set by means of the magnetization change across the I transmission encoding steps. Encoding according to the transmission encoding scheme therefore comprises amplitude encoding by varying the amplitudes of transverse magnetization across the I encoding steps. One possible variant for such an amplitude encoding for N subvolumes would be to set an amplitude A1 of transverse magnetization in a different subvolume in each encoding step of the transmission coding scheme and to set an amplitude A2 that differs from A1 in the remaining subvolumes.

An alternate variant is especially preferred, in which the transmission encoding scheme only defines the phase of the transverse magnetization to be set spatially dependently by means of the magnetization change across the I transmission encoding steps. Encoding according to the transmission encoding scheme A therefore then comprises phase coding by varying the phases of transverse magnetization across the I encoding steps. One possible variant for such a phase encoding for N subvolumes would be to set a phase P1 of transverse magnetization in a different subvolume in each encoding step of the transmission encoding scheme and to set a phase P2 that differs from P1 in the remaining subvolumes.

A variant especially preferred for practical use of the inventive method is provided if the entire mapping volume is an unconnected region. An interesting example of this variant is the simultaneous mapping of RoIs that are relatively widely dispersed and relatively small with respect to the size of the volume under examination.

The inventive method provides especially great advantages if the mapping volumes are limited to the size definitely required for the measurement task. If the measurement effort for executing the reception encoding scheme for a specific spatial resolution is reduced by limiting it to the actual RoIs, the measurement time can be considerably reduced.

In a simple variant of the inventive method, one and no more than one mapping volume is selected. For many imaging tasks, this will be the most interesting application of the inventive method.

The inventive method can be used very effectively if multiple mapping volumes are to be measured simultaneously. For example, by adapting the reception encoding scheme to the largest of these mapping regions while simultaneously using the same reception encoding steps, a signification measurement time reduction can be achieved for all mapping volumes. In an alternative variant, two mapping volumes are therefore selected and each of these mapping volumes is uniquely spatially encoded with the reception encoding scheme, not however the union of the mapping volumes.

Use of multiple reception elements to receive the MR signals can be advantageous in terms of the resulting image quality and reducing the measurement time. In particular, these advantages can be exploited by using parallel imaging techniques.

A further, especially advantageous variant of the inventive method uses the change in magnetization with at least two transmission elements. The radio-frequency pulses are therefore applied with more than one transmission element of a transmission antenna device. By using a plurality of transmission elements, it is possible to improve the spatial selectivity of the radio-frequency pulses. This can result in improved spatial definition of the subvolumes and/or—in the case of multidimensional RF pules—a reduction of the RF pulse lengths.

An especially preferred variant of the inventive method is characterized in that, in the preparation step, temporally and spatially varying additional magnetic fields, which are produced with a gradient system and act during irradiation of the RF pulse or RF pulses to be irradiated to effect the magnetization change, are defined and, for these additional magnetic fields for each of the I transmission encoding steps of the transmission encoding scheme, the temporal amplitude and phase profile of the RF pulses to be irradiated to effect the magnetization change is calculated, and that, in the execution step, the RF pulses thus calculated are applied during the action of these additional magnetic fields. The radio-frequency pulses are therefore combined with spatially and temporally varying additional magnetic fields, which are superimposed on the static and homogeneous magnetic basic field of a magnetic resonance apparatus oriented in the z direction. The use of additional magnetic fields is one of several variants for providing the radio-frequency pulses with spatial selectivity.

In a further very important variant of the inventive method, at least one of the subvolumes is adapted to the anatomical, morphological, or functional conditions of the object under examination. It is particularly advantageous if the corresponding mapping volume(s) can be reduced to the minimum size needed for the measurement task, wherein the measurement time is generally reduced for a defined spatial resolution. Moreover, in this way certain regions of the object under examination that might cause interference in the measurement can be excluded from excitation by positioning them in a subvolume that is assigned to the outer volume. Such a subvolume to be excluded can also be defined inside the mapping volume.

In special variants of the inventive method, determining the allocation of the magnetic resonance signals to subvolumes is performed by means of one-, two-, or three-dimensional Fourier transformation or Hadamard transformation or wavelet transformation.

Moreover, it is also possible to set the same flip angle everywhere in all encoding steps using the change in magnetization for at least one subvolume (SV1, SV2). The magnetization change is therefore defined in all encoding steps in such a way that, within at least one subvolume, the same flip angle is set throughout. In this way, falsification of the acquired image due to the transmission characteristics of the transmission antenna facility, for example, in the form of local highlighting and shading, can be suppressed.

In a very interesting and advantageous variant of the inventive method, in all encoding steps, by means of the spatially selective RF pulses effecting the magnetic change, in at least two subvolumes, different characteristics of the MR signal are defined beyond the different encoding according to the transmission encoding scheme. The spatially selective RF pulses used for transmission encoding are therefore used to set different characteristics of the MR signal in different subvolumes. As a rule, this is done using targeted spatially dependent definitions for the setting of the amplitude of the transverse magnetization caused by the change in magnetization. For example, in the inner and outer volumes, it is possible to specifically set a different steady state of magnetization or, despite different local relaxation times of the mapping object in the inner an outer volume, as similar a steady state magnetization as possible, which can then result in a varying contrast response in the acquired images or to differing qualities of suppression of the signals coming from the outer volume. The setting of different image contrasts in the different mapping volumes can provide very useful additional information about the object under examination. A detailed description of this is to be found in the patent application submitted by the same applicant on the same day entitled: "Method for generating a desired temporal profile of the magnetization state in an object under examination during an experiment involving magnetic resonance."

The inventive method assumes that a particular MRI measurement task is to be solved, which initially results from the fact that in an object under examination, which is located inside the measurement volume of an MR apparatus, certain RoIs that are located in previously definable subvolumes are to be mapped with a particular predefined measurement sequence with which, for example, desired image contrasts can be realized. For efficiency reasons, as far as possible only these subvolumes, the so-called mapping volumes, are to be mapped.

The measurement sequence itself can already be designed in such a way that, for example, by means of slice selection only certain partial regions contribute to the acquired MR signals. Multi-dimensionally spatially selective RF pulses as a component of the measurement sequence can also delimit the region contributing signals. The volume characterized by such characteristics of the measurement sequence, from which nuclear spins excited during the measurement sequence contribute to at least one thus acquired MR signal directly used for image reconstruction, is called the examination volume. It is assumed that, during application of the measurement sequence, this examination volume was usually defined based on so-called pilot acquisitions, as part of the conditions resulting from the measurement sequence and the MR apparatus and of the expected image quality in terms of size, shape, and position, normally by appropriate parameterization of the measurement sequence, such that it contains all regions of interest for the acquisition of the object under examination.

For the selected RoIs, subvolumes that contain the RoIs are now defined in the preparation step. If the outer volume, that is, the volume that is complementary to the mapping volume within the volume under examination, is now completely covered by one or more further subvolumes, all MR signals from the volume under examination that contribute to the measurement can be assigned to exactly one of the subvolumes defined in this way. It is advantageous for the measurement duration to define precisely one subvolume to cover the outer volume. The subvolumes can extend beyond the volume under examination because they are in any case effectively limited to the region that can be excited by the transmission elements.

An important characteristic of the inventive method is that the spatially selective RF pulses contained in each encoding step of the measurement sequence, in addition to the task of applying the transmission encoding, can also implement further special characteristics of the measurement sequence. Such a characteristic is the contrast response of the measurement sequence, which can be additionally set spatially dependently via these RF pulses, for example, by achievable spatially dependent setting of the flip angle. An important application is B1 shimming inside the volume under examination. Another object that can also be achieved with the RF pulses—simultaneously with the transmission encoding—is adaptation of the volume under examination to prescribed one-, two- or three-dimensional masks, outside of which the amplitude of the transverse magnetization is to be set to zero. Definitions of this kind for the spatially selective RF pulses, which go beyond the encoding definitions, for example, spatial masks or cards of transverse magnetization or spatial patterns of the contrast to be achieved, are considered characteristics of the measurement sequence and influence, among other things, the definition of the volume under examination. So besides the transmission encoding definitions possibly additional definitions of additional measurement sequence characteristics are included in the calculation of the RF pulses.

Whenever calculation of the RF pulses for a desired change in magnetization is mentioned, it is important to remember that a change in magnetization can also be implemented by multiple temporally consecutive irradiated RF pulses and that, in this calculation, all RF waveforms that are irradiated from various transmission elements must be defined for each one of these RF pulses. One RF pulse comprises at least one RF waveform, wherein each waveform has a certain amplitude and phase profile over time and is irradiated by one and no more than one transmission element. Each encoding step can therefore have multiple sets of RF waveforms, which must be irradiated accordingly. The change in magnetization that this causes is then the spatially dependent change in amplitude and/or phase of the transverse magnetization achieved after the last RF pulse has ended in each encoding step.

The selected reception encoding scheme typically contains one or a combination of several of the usual spatial encoding methods, i.e. frequency, phase and/or sensitivity encodings. The limiting case of pure frequency encoding is implemented in back projection imaging. The limiting case of pure sensitivity encoding is achieved with the use of very many reception elements, wherein a single reception encoding step is sufficient (massively parallel imaging). Pure phase encoding schemes are used, for example, in chemical shift imaging.

An essential aspect of the inventive method is that the reception encoding scheme does not have to be so complex that the entire volume under examination is spatially encoded, but just the mapping volumes.

In the simplest case, only one subvolume has to be mapped and a second subvolume covers the outer region of this mapping volume, as shown in FIG. 2a. If this mapping volume is now spatially encoded in at least one spatial direction using classic Cartesian phase encoding, the advantage of reducing the measurement duration with the same spatial resolution is achieved by "saving" phase encoding steps. If the volume under examination has a maximum extent in the phase encoding direction, which is a factor f larger than the maximum extent of the mapping volume in this direction, the measurement duration can be reduced to the fraction 2/f. The factor 2 is derived from the fact that 2 transmission encoding steps are required. For phase encoding in three dimensions in this case, the measurement time can be reduced by the factor f1*f2*f3/2, wherein f1, f2, f3 are the respective reduction factors of the extents of the region to be encoded for the three phase encoding directions.

If multiple mapping volumes are mapped simultaneously, as described in FIG. 2b, a measurement time advantage can be achieved by using the same phase encoding steps in order to spatially encode multiple mapping volumes in the same spatial direction. If the FoV is the largest extent in the phase encoding direction of the mapping volume that is largest in this respect, all other mapping volumes can be additionally encoded with a phase encoding scheme defined for this FoV because the phase encoding is translationally invariant. If MR signals are received from a region which has the maximum extent FoV in the phase encoding direction, the position coordinates can be uniquely assigned in this direction irrespective of where this region is positioned in the phase encoding direction. In the inventive method, the additional transmission encoding ensures unique assignment of components of acquired signals to the mapping volume and the phase encoding scheme for the spatial resolution in each FoV.

If the FoV has a reduction factor f as compared with the extent of the volume under examination in the phase encoding direction, and if M equally sized mapping volumes are acquired simultaneously in this direction, and if the outer volume is covered by a single subvolume, a measurement time modified by the factor (M+1)/f results for the encoding direction relative to the measurement duration for the total volume, i.e. a measurement time reduction only occurs if a correspondingly small FoV is chosen.

Unlike the known methods [1], in this method it is not mandatory to suppress MR signals from the outer volume using spatially selective RF pulses generating transverse magnetization which vanishes there in all spatial encoding steps. Because in the inventive method, however, spatially selective RF pulses are irradiated in each encoding step, this characteristic of the known method can be simultaneously realized in the performance of the same measurement sequence. This is the case if definition of the change in magnetization to be effected with the spatially selective RF pulse(s) includes generation of vanishing transverse magnetization in certain areas of the object under examination. Both methods are by no means mutually exclusive and can be advantageously combined, for example, if, during simultaneous occurrence of different imperfections of the apparatus and/or object-related disturbances, one or the other method of spatially dependent exclusion of MR signals from image reconstruction is more efficient.

With respect to the encoding steps performed in the execution step, it should be emphasized that encoding characteristics of both the transmission encoding scheme and the reception encoding scheme are superposed onto the acquired MR signal, wherein both encoding schemes define the systematic nature of the changes from encoding step to encoding step.

It can be advantageous if before execution of the encoding steps the nuclear spin system is changed to a steady state, for example, by repeated execution of an encoding step of the execution step without data acquisition or data utilization. It can be advantageous for the image quality if spoiler gradients are used in each encoding step, to dephase any disturbing residual transverse magnetization.

In a result step, the results of reconstruction and/or derived quantities are then stored and displayed. Preferably, two- or three-dimensional images, which render certain characteristics of the magnetic resonance signals, are displayed encoded in colors or gray-scale values. Integrated representation of all mapping volumes related to a common reference system is of particular interest.

Further advantages result from the description and the drawings. Moreover, the features stated above and further below can be used inventively singly or together in any combination. The embodiments shown and described are not intended to be an exhaustive list, rather are examples to explain the invention.

The invention is shown in the drawings and is explained in more detail by way of embodiments.

The figures show:

BRIEF DESCRIPTION OF THE DRAWING

FIG. 4 an MR overview image with a water bottle as the object under examination and with subvolumes drawn in;

FIG. 5 a suitable amplitude and phase distribution of the transverse magnetization for transmission encoding steps 1 and 2 according to the transmission encoding scheme for spatial encoding;

FIG. 6 a schematic representation of the sequence of gradients and RF pulses in the encoding steps during the execution step;

FIG. 7 the experimentally determined amplitude and phase distribution of transverse magnetization realized with RF pulses according to the transmission encoding scheme;

FIG. 8 the separate representation of signals from two subvolumes; and

FIG. 9 the MR image of a segment of a tangerine implemented with a reduced reception encoding scheme and excitation encoding according to the transmission encoding scheme.

DESCRIPTION OF THE PREFERRED EMBODIMENT

Figure 1:
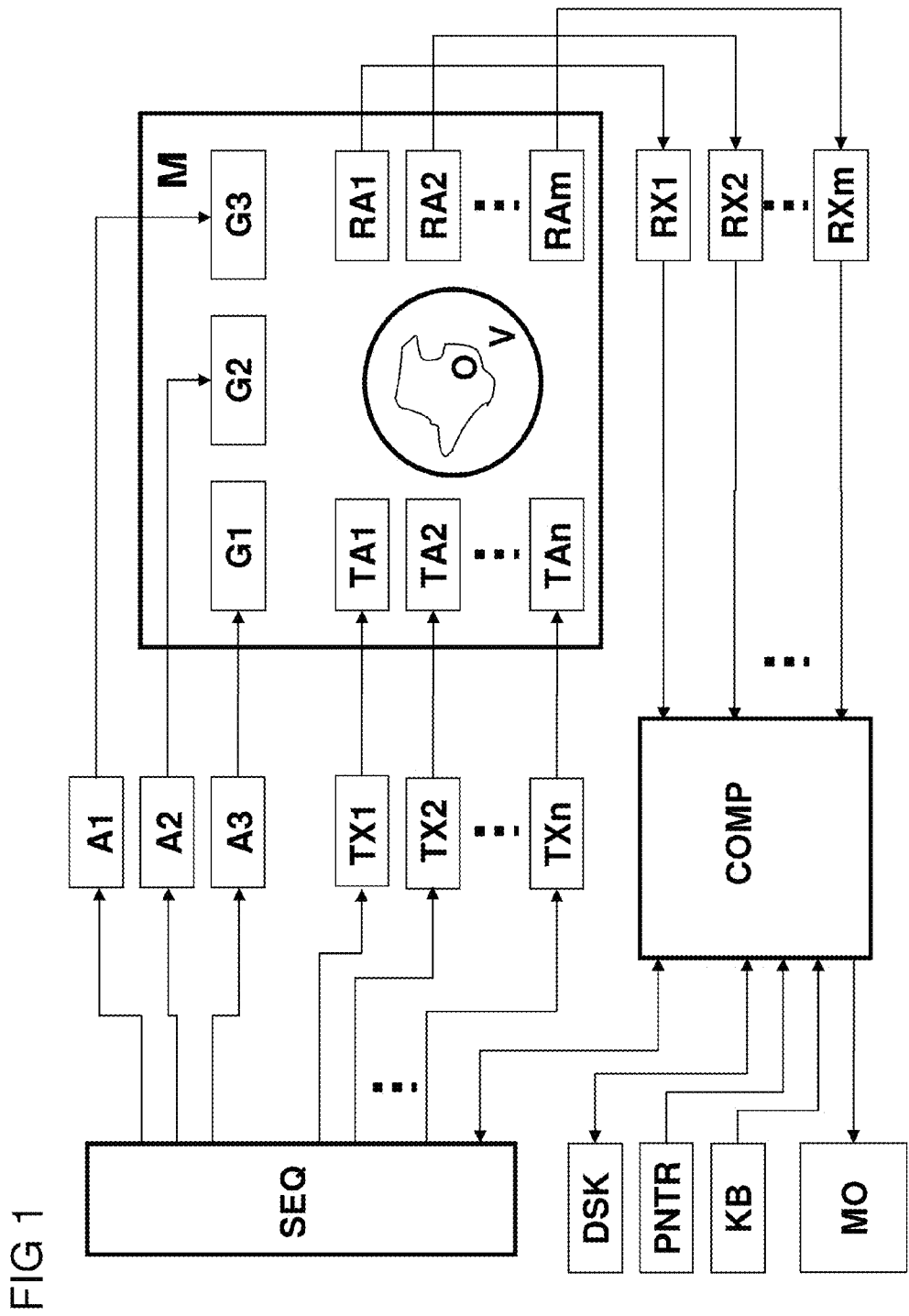
FIG. 1 a schematic representation of a magnetic resonance apparatus according to prior art suitable for performing the inventive method.

FIG. 1 schematically shows a magnetic resonance apparatus that is suitable for performing the inventive method. The apparatus contains a main magnet M, with which the essentially homogeneous and static basic magnetic field is produced in a measurement volume V. The part of the object under examination that is contained in the measurement volume will subsequently be referred to as the object under examination or simply the object O. Surrounding the measurement volume V, a gradient system is put into the bore of the main magnet M with which different variants of additional magnetic fields can be implemented by connecting coils, usually a plurality of coils, to form coil combinations G1, G2, G3, . . . . FIG. 1 shows an example of three such coil combinations, G1, G2, and G3. With the gradient system, additional magnetic fields of controllable duration and strength can be superimposed on the basic field. With gradient amplifiers A1, A2, A3, that are controlled by a sequence control unit SEQ to produce gradient pulses at the right instant, the gradient coils sets G1, G2, and G3 are supplied with electric power to produce the additional fields.

Within the gradient field system, there are multiple transmission elements, TA1 to TAn, which are together termed the transmission antenna device. They surround an object under examination O and are powered from multiple independent RF power transmitters TX1 . . . TXn. The RF waveforms produced by these RF power transmitters TX1 . . . TXn are determined by the sequence control unit SEQ and triggered at the correct time. With the transmission elements TA1 to TAn, RF waveforms are irradiated onto the object under examination O in the volume under examination V, where they excite nuclear spins. The magnetic resonance signals caused by this are converted into electrical voltage signals with one or more RF reception elements RA1, . . . , RAm and are then fed into a corresponding number of reception units RX1, . . . , RXm. The reception elements RA1, . . . , RAm are together termed the reception antenna equipment consisting of m reception elements RA1, . . . , RAm. They are also located within the gradient coils G1, G2, G3, and surround the object under examination O.

To reduce the complexity of the apparatus, the transmission and reception antenna devices can be designed and connected in such a way that one or more of the transmission elements TA1 to TAn are also used to receive the magnetic resonance signals. In such a case, which is not shown in FIG. 1, switchover between transmission and reception modes is assured by one or more of the electronic transmission-reception switches controlled by the sequence control unit SEQ, that is, that during the RF transmission phases of the executed pulse sequence, this antenna or these antennas are connected with the corresponding RF power transmitter or transmitters and disconnected from the allocated reception channel or channels, while, for the reception phases, transmitter disconnection and reception channel connection is performed.

With the reception units RX1 to RXm shown in FIG. 1, the signals received are amplified and converted to digital signals using known signal processing methods and passed on to an electronic computer system COMP. In addition to reconstruction of images and spectrums and derived quantities from the measured data received, the control computer system COMP is used to operate the entire MR measurement apparatus and to initiate execution of the pulse sequences by appropriate communication with the sequence control unit SEQ. User-guided or automatic execution of programs for adjusting the measurement apparatus characteristics and/or for generating magnetic resonance images is also performed by this control computer system COMP, as are visualization of the reconstructed images and storage and administration of the measurement and image data and control programs. For these tasks, this computer system is equipped with at least one processor, a working memory, a computer keyboard KB, a pointing device PNTR, for example, a computer mouse, a monitor MON, and an external digital storage unit DSK.

An explanation of how the inventive method can be performed with such an MR measurement apparatus is given below based on specific examples. In the presentation of these examples, eight transmission elements were used, which are simultaneously used as reception elements.

Figure 2:
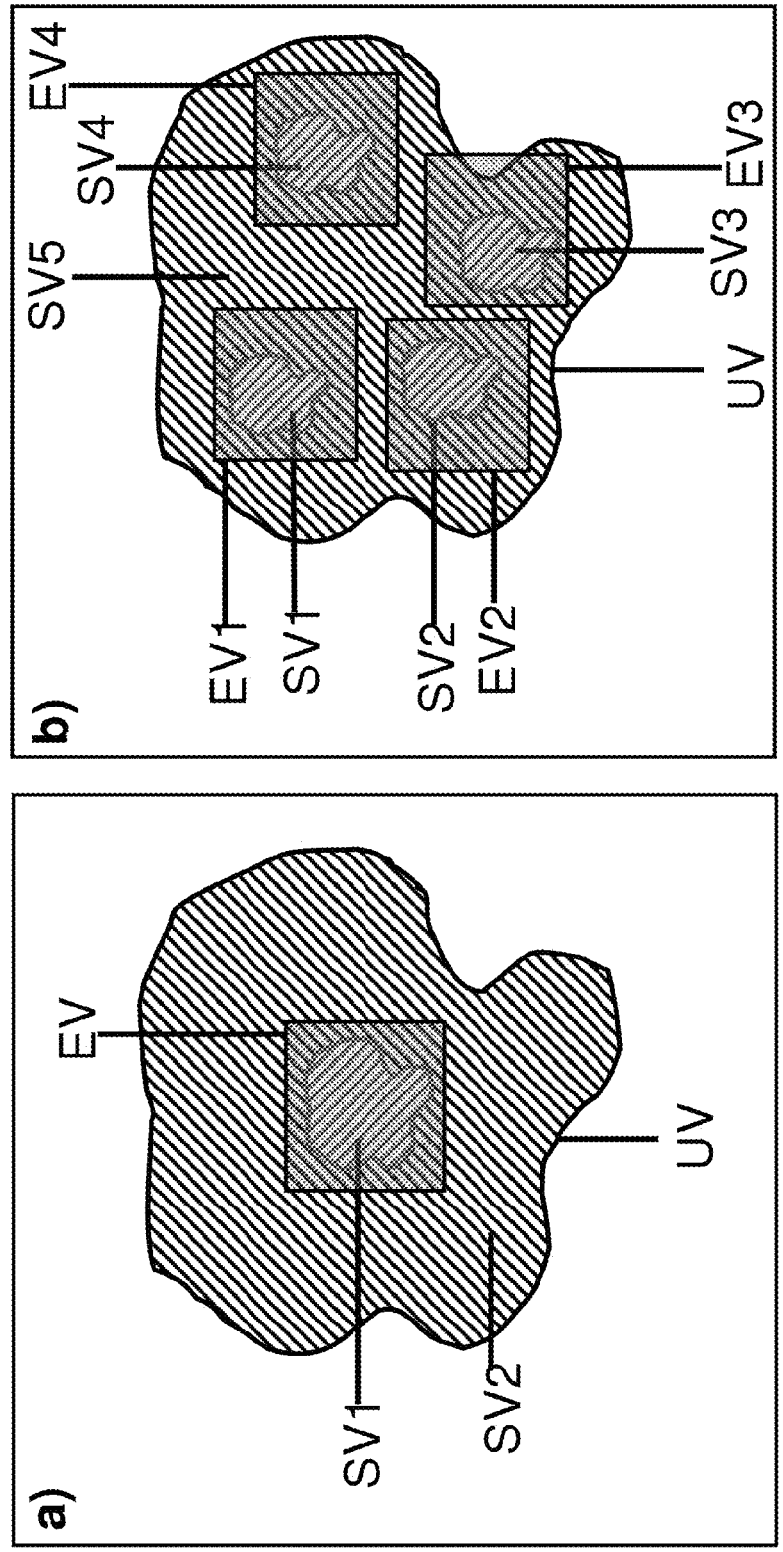
FIG. 2 a schematic representation of especially preferred measurement topologies.

FIG. 2 schematically illustrates two especially preferred measurement topologies for the inventive method, wherein the figures can be interpreted as direct representations of a two-dimensional reception encoding scheme or as cross-sectional representations of a three-dimensional reception encoding scheme. FIG. 2a illustrates the mapping of a single subvolume SV1, i.e. SV1 represents a mapping volume and the inner volume, while another subvolume SV2 corresponds to the outer volume. SV1 and SV2 completely cover the volume under examination UV. The reception encoding scheme is designed in such a way that it spatially encodes uniquely in volume EV. In FIG. 2b, SV1, SV2, SV3, and SV4 represent the mapping volumes that together define the inner volume, while SV5 represents the outer volume, which is not to be mapped. In this case, the reception encoding scheme in volumes EV1, EV2, EV3, and EV4 permit unique spatial encoding, wherein, in the present example, these volumes are identical in size.

The examples described below have the measurement topology shown in FIG. 2a.

Figure 4:
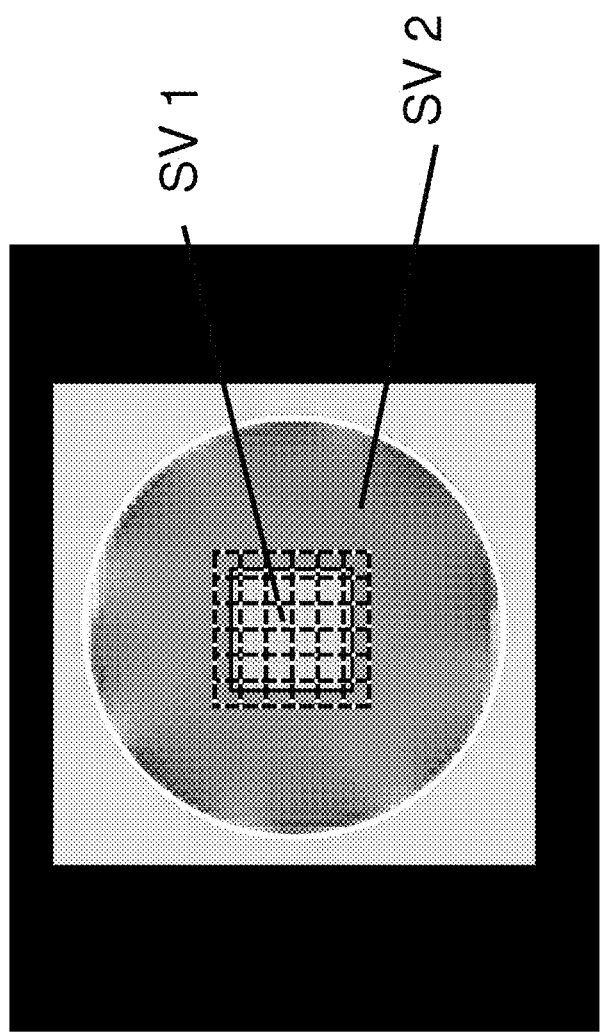

Firstly, execution of a transmission encoding, implemented specifically here as excitation encoding, is described for two subvolumes by means of an imaging experiment, in which a water-filled bottle was used as the object under examination (FIG. 4). Then the inventive method is applied to map a single segment of a tangerine (FIG. 9) using the same procedure, wherein this segment was covered by a subvolume and the remainder of the tangerine was acquired in an additional subvolume that defines the outer volume. The experiments described are three-dimensional imaging experiments, wherein only individual slices of the reconstructed data sets are represented in the illustrations.

Figure 3:
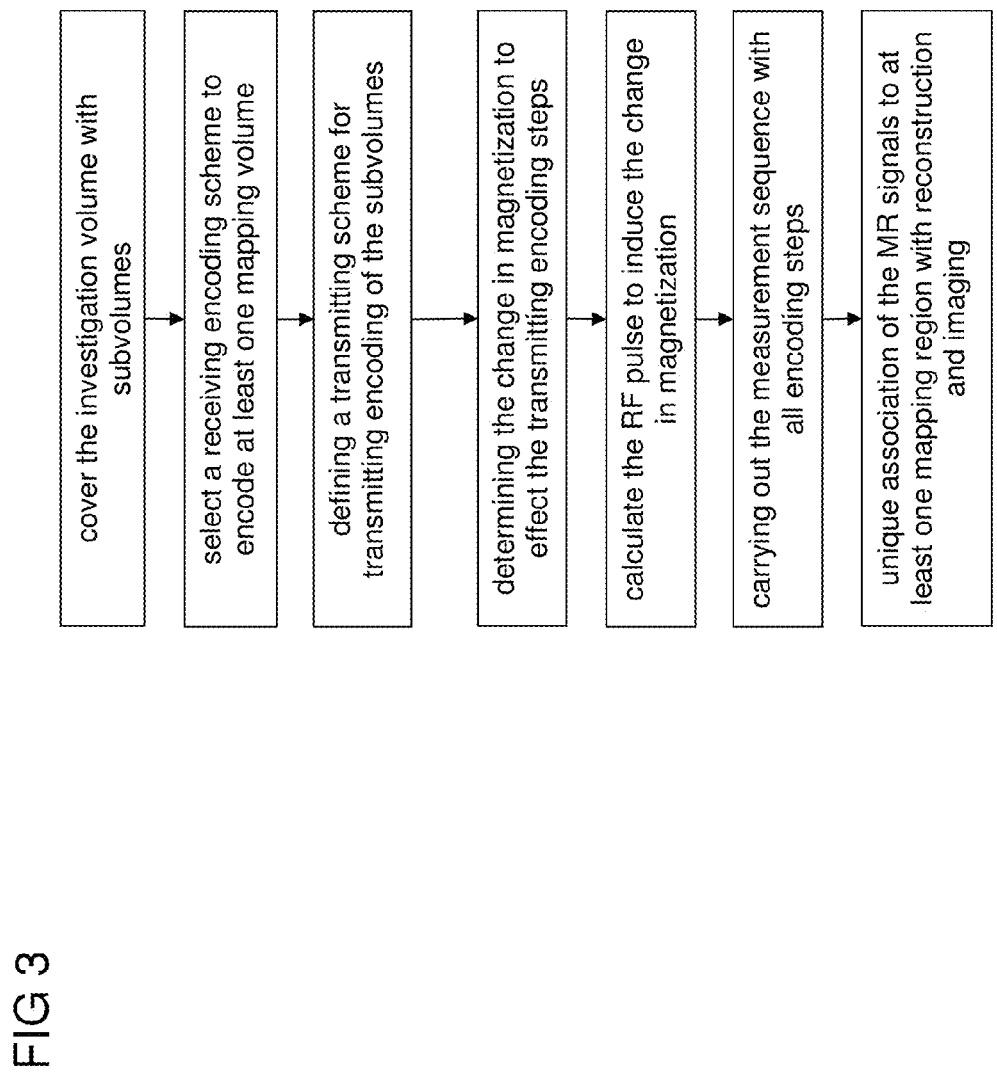
FIG. 3 a flow chart of a possible sequence of the inventive method.

FIG. 3 schematically shows the sequence in which the examples are performed.

In both examples, the sequence starts by choosing two subvolumes, which together entirely cover the volume under examination. These were defined in both cases based on a previously acquired overview image acquired in an MR experiment, from which the delimitation of the volume under examination can be seen. It is important to ensure that the subvolumes do not overlap and are preferably slightly larger than the volume under examination, to avoid the precondition of full coverage of the volume under examination being violated by imprecisions in the geometrical delimitation.

FIG. 4 shows the selection of a cuboid inner subvolume SV1 for the first example and an outer subvolume SV2, which fully surrounds the inner subvolume SV1. In principle, both subvolumes SV1, SV2, can be any shape, an aspect which is better demonstrated by the example of a tangerine segment. In this example, subvolume SV1 is selected as a mapping volume and therefore an inner volume from which an image is to be generated.

For this, a three-dimensional reception encoding scheme is defined in such a way that using frequency and phase encoding, which is implemented by creating additional magnetic fields, MR signals that are derived from the subvolume SV1 are fully and uniquely three-dimensionally spatially encoded.

For this, the duration and amplitude of the gradient pulses $G_x$, $G_y$, $G_z$, which are generated by gradient coils G1, G2, and G3 are determined and the number of encoding steps in this example is defined as K=64×64, so that the desired volume is encoded with the desired resolution.

Because the reception encoding scheme specified in this way is uniquely spatially encoded in SV1 but not for the entire volume under examination, MR signal components that occur outside the reception encoding region create artifacts in the image of subvolume SV1. In the spatial direction, in which frequency encoding is performed, this can be avoided by frequency-selective filtering of the acquired signal. This does not work in the phase encoding directions.

According to the invention, therefore, a second encoding scheme, the transmission encoding scheme is defined to differentiate signals from subvolumes SV1 and SV2, which is achieved by irradiating spatially selective RF pulses.

In order to differentiate between signals from the two subvolumes SV1 and SV2, the simplest form of a Fourier encoding scheme with I=2 transmission encoding steps is used, in which the transverse magnetization phase is varied. FIG. 5 shows that the amplitude of the transverse magnetization in both transmission encoding steps is kept constant by defining a thoroughly homogeneous flip angle of 8° across all transmission encoding steps, while the phase distribution is varied. The transverse magnetization generated in the experiment can have any phase distribution in the first transmission encoding step, which is used as a reference for the second transmission encoding step and is assumed by definition to be homogeneously 0°. In the second transmission encoding step, the transverse magnetization phase within SV1 relative to this reference is 0° while, in SV2, it is to assume a value of 180°.

In this example, therefore, only the transverse magnetization phase is varied. However, it is not absolutely necessary to define an homogeneous flip angle for the entire examination volume. Rather it is possible to define different homogeneous flip angles within each of the subvolumes SV1 and SV2. For example, it can be advantageous to excite the mapping volume with a flip angle, which achieves (on average) an MR signal maximum (called Ernst angle), while the outer volume is excited with a flip angle, in which imperfections of the excitation only have a slight effect on the resulting MR signal strength. In this way, the intended MR signal separation with respect to subvolumes SV1 and SV2 can be performed with greater precision.

In these examples, the transmission encoding is implemented by irradiation of spatially selective excitation pulses and the flip angle and phase patterns illustrated in FIG. 5 show the requirements for the change in magnetization for each transmission encoding step. Although the requirements geometrically extend beyond the volume under examination, they are not applied outside the volume under examination because, for example, no nuclear spins exist there or they lie outside the region of sensitivity of the transmission antenna equipment.

In the examples, PEX pulses are used as spatially selective RF pulses to achieve the change in magnetization, i.e., multiple channel RF pulses, which in combination with gradient pulses, are irradiated via a corresponding number of transmission elements, eight in our examples. Because spatially linear gradient fields are used, the gradient pulses deployed can be represented as a k-space trajectory, which, in this case, exhibits a progression of spirals stacked one on top of the other. Due to the undersampling of the k-space trajectory resulting from the additional sensitivity encoding of the transmission elements, the length of the excitation pulses could be reduced by a factor of 4 as compared with single-channel transmission.

The phase and amplitude profile of the two required RF pulses for implementing the change in magnetization according to the selected transmission encoding scheme is calculated using a method according to [8], wherein the targeted change in magnetization, the spiral-shaped k-space trajectory, and the transmission profiles of the 8 transmission elements used are included in the calculation.

In the example, an imaging experiment now follows in the form of a so-called gradient echo experiment, whose operating sequence is schematically represented in FIG. 6. The plotted gradient waveforms for spatial RF pulse encoding and the RF waveforms, in particular, are only schematic and do not provide a precise rendition of the waveforms actually used.

The first excitation is performed according to transmission encoding step 1 with the first of the calculated PEX pulses. Then spatial encoding is performed according to reception encoding scheme 1 with phase gradients in the y and z direction. Another component of the reception encoding scheme is encoding in the x direction using a readout gradient, which is applied while the MR signals are acquired. This procedure is repeated for each reception encoding step as a loop S1, wherein the amplitude of the phase gradients is varied. This entire procedure is then repeated again for each transmission encoding step as loop S2, wherein the corresponding RF pulses are applied. The sequence in which the loops are executed is not important. It is merely necessary to ensure that every encoding step combination of reception and transmission encoding scheme is executed. Data reconstruction must be adapted to the sequence in which the encoding steps are executed.

The data acquired in loop S1 can either be reconstructed separately from those in loop S2 as individual images, in this case by means of three-dimensional Fourier transformation, or combined in a signal reconstruction step by means of four-dimensional Fourier transformation.

FIG. 7 shows the reconstruction result of the two data sets acquired in loop S1. Please note that, unlike in the inventive method, a reception encoding scheme, which encodes the volume under examination uniquely and in full was used here in order to visualize the working principle of the transmission encoding scheme for acquiring these data sets. The amplitudes and phases of the transverse magnetization essentially show the profiles as defined in FIG. 5 (weighted with the reception profiles of the reception elements). In the simple case of Fourier encoding used for the transmission encoding scheme, the signals from SV1 and SV2 can now be simply separated by adding and subtracting the complex data sets.

Adding the data sets results in the addition of the signal amplitudes in SV1, and the phase difference during excitation according to the transmission encoding scheme results in the subtraction and cancellation of the signal amplitudes in SV2. Conversely, subtracting the data sets results in cancellation in SV1 and addition of the signal amplitudes in SV2. The signal distribution for SV1 and SV2 is shown in FIG. 8. The MR signals from the inner volume are thus clearly separated from those from the outer volume.

Although the total measurement time increases with each transmission encoding step, the resulting ratio of desired signal to noise per unit time remains unchanged because, when the data are reconstructed, the correlated desired signals from the individual encoding steps increase while uncorrelated noise is reduced by averaging effects.

FIGS. 7 and 8 show reconstructed images of the first example, which, in order to demonstrate the transmission encoding scheme, were acquired with a reception encoding scheme that uniquely encodes the entire volume under examination. In the second example, in which a tangerine was used as the object under examination, in accordance with the inventive method the volume encoded with the reception encoding volume was chosen to be considerably smaller than the volume under examination, as illustrated in FIG. 9.

FIG. 9a shows an overview image of the tangerine, in which the two subvolumes, the mapping volume SV1 and the outer volume SV2, as well as the volume uniquely encoded by the reception encoding scheme are drawn in.

FIGS. 9b and c show the images acquired in transmission encoding steps 1 and 2 and reconstructed according to the reception encoding scheme, which clearly show artifacts caused by the non-unique reception encoding in the volume under examination. Only the separation of the signals by MR signals from subvolumes SV1 and SV2 according to the transmission encoding scheme produces an artifact-free image of subvolume SV1, as shown in FIG. 9d.

By reducing the encoding region of the reception encoding scheme while retaining the same number of encoding steps, in this case the resolution in FIG. 9d could be increased over FIG. 9a without having to increase the measurement time.

The number of encoding steps can also be reduced in an analogous manner to acquire the data in a shorter measurement time while retaining the spatial resolution. A combination of increased resolution and shorter measurement time is also possible.

LIST OF REFERENCE SYMBOLS

A1, A2, A3 Gradient amplifier
COMP Computer system
DSK Storage unit
EV, EV1 . . . 4 Volumes in which the reception encoding scheme is uniquely spatially encoded
G Housing
G1, G2, G2 Gradient coils
$G_x$, $G_y$, $G_z$ Gradient fields
KB Computer keyboard
M Main magnet
MO Screen
O Object under examination
PNTR Pointing device
RA1 . . . M RF reception elements
RX1 . . . M Reception units
SEQ Sequence control unit
SV1 . . . 5 Subvolume
TA1 . . . N RF transmission elements
TX1 . . . N RF power transmitter
V Measurement volume
UV Volume under examination

REFERENCES

[1] Feinberg D A, Hoenninger J C, Crooks L E, Kaufman L, Watts J C, Arakawa M. *Inner Volume MR Imaging: Technical Concepts and Their Application.* Radiology 156 (1985), pp. 743-747.
[2] Glover G H. *Phase-offset multiplanar (POMP) volume imaging: a new technique.* J Magn Reson Imaging 1 (1991) pp. 457-461
[3] Pauly J, Nishimura D, Macovski, A. *A k-space analysis of small-tip-angle excitation.* Journal of Magnetic Resonance 81 (1989), pp. 43-56.
[4] Ullmann P, Schneider J T, Haas M, Wissmann R, Ruhm W. *Single-And Multi-Voxel MR-Spectroscopy Using Parallel Excitation.* Proc 17th Scientific Meeting, Intl Soc Magn Reson Med, Honolulu (2009), p. 2602
[5] DE 10 2007 044 463 B4
[6] Katscher U, Börnert P, Leussler C, van den Brink J S. *Transmit SENSE.* Magnetic Resonance in Medicine 49 (2003), pp. 144-50.
[7] Seifert F, Wuebbeler G, Junge S, Rinneberg H. B1(+) steering by an adaptive 4-channel transmit/receive coil array. Proc 12th Scientific Meeting, Intl Soc Magn Reson Med, Kyoto (2004), pp. 1569.
[8] Grissom W, Yip C-Y, Zhang Z, Stenger, V A, Fessler J A, Noll D C. *Spatial domain method for the design of RF pulses in multicoil parallel excitation.* Magnetic Resonance in Medicine 56 (2006), pp. 620-629.

We claim:
1. A method for determining a spatial distribution of magnetic resonance signals from at least one of N non-overlapping subvolumes of an object under examination in a measurement volume of a magnetic resonance apparatus, wherein N≥2, the method comprising the steps of:
a) executing a preparation step, the preparation step comprising:
a1) selecting a measurement sequence with encoding steps, wherein each encoding step includes irradiation of one or more spatially selective RF pulses to effect one magnetization change in each encoding step;
a2) selecting the N subvolumes such that, taken together, those subvolumes completely cover at least one volume under examination, the volume under examination corresponding to a part of the object under examination in which nuclear spins excited during execution of the selected measurement sequence contribute to at least one of acquired MR signals;
a3) selecting a reception encoding scheme with K reception encoding steps, wherein K≥1, the reception encoding scheme defining unique spatial encoding in at least one spatial dimension for at least one of the subvolumes, wherein that spatial encoding is not unique for an entire volume under examination in at least one spatial dimension;
a4) defining a transmission encoding scheme with I transmission encoding steps, wherein I≥N≥2, wherein encoding is effected via an amplitude and/or phase of transverse magnetization defined spatially dependently by means of a magnetization change, wherein, for each of the I transmission encoding steps, the magnetization change is defined such that, at no position within each subvolume, a same encoding is defined as at another position within another subvolume, with excited nuclear spins contributing to an acquired magnetic resonance signal in at least one transmission encoding step and in at least two of the subvolumes; and
a5) calculating a temporal amplitude and phase profile of the spatially selective RF pulses to be irradiated to effect the magnetization changes;
b) carrying out an execution step for all encoding steps, each reception encoding step that is defined according to the reception encoding scheme being executed I times with variations according to the I transmission encoding steps of the transmission encoding scheme, wherein, in each encoding step, all RF pulses calculated for each transmission encoding step of the transmission encoding scheme are applied by means of at least one transmission element and, without overlapping in time with those RF pulses, a spatial encoding is effected according to a reception encoding scheme, with magnetic resonance signals being acquired by means of at least one reception element;
c) executing a reconstruction step based on the transmission encoding scheme, wherein components of the acquired magnetic resonance signals are assigned to the N subvolumes and, for at least one of the subvolumes spatially encoded according to the reception encoding scheme, one or more spatial distributions of the mag- netic resonance signals is reconstructed from the acquired magnetic resonance signals and/or variables derived therefrom are calculated, wherein this or these subvolumes are designated mapping volumes; and d) executing a result step in which results of the reconstruction step are stored and/or displayed.

2. The method of claim 1, wherein the transmission encoding scheme only defines the amplitude of the transverse magnetization to be set spatially dependently by means of the magnetization change across the I transmission encoding steps.

3. The method of claim 1, the transmission encoding scheme only defines the phase of the transverse magnetization to be set spatially dependently by means of the magnetization change across the I transmission encoding steps.

4. The method of claim 1, wherein an entirety of mapping volumes is a non-contiguous region.

5. The method of claim 1, wherein at least one mapping volume is restricted to a size that is essential for a measurement task.

6. The method of claim 1, wherein only one mapping volume is selected.

7. The method of claim 1, wherein at least two mapping volumes are selected and each of these mapping volumes is uniquely spatially encoded with the reception encoding scheme, wherein a union of the mapping volumes is thereby not uniquely spatially encoded.

8. The method of claim 1, wherein reception of the magnetic resonance signals is performed by means of at least two reception elements.

9. The method of claim 1, wherein the magnetization changes are effected by means of at least two transmission elements.

10. The method of claim 1, wherein in step a), temporally and spatially varying additional magnetic fields, which are produced with a gradient system and act during irradiation of the RF pulse or RF pulses to be irradiated to effect the magnetization change, are defined and, for these additional magnetic fields for each of the I transmission coding steps of the transmission coding scheme, a temporal amplitude and phase profile of the RF pulses to be irradiated to effect the magnetization change is calculated, wherein, in step b), those RF pulses are applied during action of the additional magnetic fields.

11. The method of claim 1, wherein at least one subvolume is adapted to anatomical, morphological or functional characteristics of the object under examination.

12. The method of claim 1, wherein calculation of assignment of magnetic resonance components of the mapping volumes is effected by means of Fourier transformation, Hadamard transformation or wavelet transformation.

13. The method of claim 1, wherein, in all encoding steps and for at least one subvolume, a same flip angle is set everywhere to effect the change in magnetization.

14. The method of claim 1, wherein, in all encoding steps and by means of the spatially selective RF pulses effecting the magnetic change, different characteristics of the MR signal are defined in at least two subvolumes in addition to the different encoding in accordance with the transmission encoding scheme.

* * * * *